(12) United States Patent
Higuchi

(10) Patent No.: US 6,905,653 B1
(45) Date of Patent: Jun. 14, 2005

(54) ION ACTIVITY MEASURING DEVICE AND METHOD FOR PRODUCING THE SAME

(76) Inventor: Yoshihiko Higuchi, c/o Kyoto Daiichi Kagaku Co., Ltd., 57, Nishiaketa-cho, Higashikujo, Minami-ku, Kyoto-shi, Kyoto-fu (JP)

( * ) Notice: Subject to any disclaimer, the term of this patent is extended or adjusted under 35 U.S.C. 154(b) by 0 days.

(21) Appl. No.: 09/473,165

(22) Filed: Dec. 28, 1999

Related U.S. Application Data (62) Division of application No. 08/959,125, filed on Oct. 28, 1997, now abandoned.

(30) Foreign Application Priority Data

Oct. 31, 1996 (JP) .............................. 8-290226
Oct. 31, 1996 (JP) .............................. 8-290227

(51) Int. Cl.$^7$ ............................................. G01N 31/22
(52) U.S. Cl. .............................. 422/56; 422/57; 422/58; 422/61
(58) Field of Search ............................. 422/56, 57, 58, 422/61

(56) References Cited

U.S. PATENT DOCUMENTS

| | | | |
|---|---|---|---|
| 3,992,158 A | * 11/1976 | Przybylowicz et al. | 422/57 |
| 4,430,436 A | 2/1984 | Koyama | 436/531 |
| 4,438,067 A | * 3/1984 | Siddiqi | 422/56 |
| 4,670,381 A | 6/1987 | Frickey | 435/7.93 |
| 4,839,278 A | 6/1989 | Terashima | 435/21 |
| 5,071,746 A | * 12/1991 | Wilk et al. | 435/7.94 |
| 5,183,741 A | * 2/1993 | Arai et al. | 435/14 |
| 5,393,493 A | 2/1995 | Makino et al. | 422/56 |
| 5,460,777 A | * 10/1995 | Kitajima et al. | 422/56 |
| 5,589,347 A | * 12/1996 | Arai et al. | 435/11 |

FOREIGN PATENT DOCUMENTS

| JP | 162302 | 11/1985 |
|---|---|---|
| JP | 449017 | 10/1991 |

* cited by examiner

Primary Examiner—Jill Warden
Assistant Examiner—LaToya Cross
(74) Attorney, Agent, or Firm—Kilpatrick Stockton LLP (57) ABSTRACT

Determining a substance to be measured in a liquid sample by measuring the degree of coloring obtained when the substance is subjected to coloring reaction in terms of reflectance. Polymer beads embedding light reflective particles are contained in a reagent layer of the dry measuring test device, or a light blocking layer containing light blocking particles, preferably polymer beads embedding the light blocking particles, is laminated on the reagent layer of the dry measuring test device. The reagent layer comprises a reagent containing a chromogen and a matrix which retains the reagent in the form of a layer, for determining the substance to be measured in the liquid sample by measuring the degree of coloring of the chromogen generated through the reaction between the substance and the reagent in terms of reflectance of light entered into the reagent layer. Speedy and highly accurate measurement is obtained in shortening measuring time by measuring reflectance corresponding to a low degree of coloring or by reducing influence of solid matter contained in the liquid sample on absorption and scattering of the measuring light and influence of external stray light entered from the opposite side of the surface of the light measuring part.

6 Claims, 3 Drawing Sheets

ION ACTIVITY MEASURING DEVICE AND METHOD FOR PRODUCING THE SAME

This application is a division of Ser. No. 08/959,125, filed on Oct. 28, 1997 now abandoned.

TECHNICAL FIELD

The present invention relates to a dry measuring test device. More specifically, the present invention relates to a dry measuring test device for determining a substance to be measured in a liquid sample by subjecting the substance to be measured to the coloring reaction and measuring the degree of coloring thus obtained in terms of reflectance, which enables speedy and highly accurate measurement.

DESCRIPTION OF THE PRIOR ART

Among the methods for determining a specific component in a liquid sample, in particular, the methods using a dry measuring test device such as test paper have been widely used at present for various purposes because the handling thereof is comparatively easy. Such dry measuring test devices basically have a structure that comprises a reagent layer having a matrix, in which a liquid sample can penetrate and be developed, containing a reagent which is soluble in the above liquid sample and reactive with the substance to be measured to generate a signal such as color, light, or the like, which can be detected and determined by analytical machines.

Among the above-described dry measuring test devices, the dry measuring test devices that determine a substance to be measured in a liquid sample through the coloring reaction between the substance to be measured and the reagent usually quantifies the substance to be measured in the liquid sample by measuring an amount of a coloring matter which is colored through the reaction of the substance to be measured with the reagent in terms of reflectance of incident light in the reagent layer. In order to conduct accurate measurement, such dry measuring test devices based on the coloring reaction contain a reflector in the reagent layer as well as the reagent for coloring. For example, the dry measuring test device described in Japanese Examined Patent Publication No. 7-21455 has a reagent layer containing not only the reagent to be used for the measurement but also, as a reflector, light-reflective water-insoluble particles, for example, white pigments such as titanium oxide, zinc oxide, barium sulfate, magnesium oxide, or the like. When the sample is whole blood, these pigments sometimes play a role of preventing red blood cells which cause measurement errors from invading the reagent layer.

However, even if the reflector is contained in the reagent layer as described above, since the reagent layer must essentially have such a structure that a sample can easily penetrate and diffuse in the layer, more specifically, it must be as thin as possible and porous, if a large amount of white pigments are contained to improve the measurement accuracy, the reagent layer becomes so dense that a liquid sample hardly penetrates it because the particle diameter of the white pigments is extremely small (0.1 to 0.3 $\mu$m). Accordingly, at the time of the measurement, penetration and development of the liquid sample proceeds slowly and it takes long time until the amount of the coloring matter generated by the reaction with the reagent becomes sufficient so as to be measurable. Thus, there is a problem in working performance.

Also, in the dry measuring test devices, a concentration condition of the reaction is considerably high, as the reagent is dissolved in the liquid sample to commence the reaction. Further, the matrix which constitutes the reagent layer usually has a structure that it easily becomes dry since its surface area contacting air is large. Although it does not matter very much when measurement is carried out by immersing the dry measuring test device in a comparatively large amount of the liquid sample, in the case of carrying out the measurement by spotting a small amount of the liquid sample, it is disadvantageous in that the measurement accuracy may possibly reduced by being affected by dryness if the measuring time is prolonged as described above.

Furthermore, if the amount of the white pigment is reduced to the extent that the reagent layer can have a porous structure, the liquid sample penetrates and is developed easily and the time required for the measurement can be shortened. However, such a reagent layer can keep high whiteness when it is dried, but light reflective efficiency becomes insufficient when the liquid sample penetrates the reagent layer, that is, at the time of measurement. As a result, the measurement is easily affected by transmission, absorption, and scattering of measuring light, or incidence of light from the outside of the test device, and the like. This is because, in the case where the reagent layer has a porous structure, an air layer incorporated therein raises light refractive index and diffused reflection light is increased, which makes apparent whiteness high when the layer is dried, while, when the layer is moisturized, moisture incorporated in the layer lowers light refractive index and transmitted light increases more than diffused reflection light, thereby reducing apparent whiteness.

Particularly, when the liquid sample contains a coloring component, for example, blood cells or the like, the component causes absorption, scattering, and the like of measuring light even if it has penetrated into the reagent layer. Alternatively, the coloring component causes absorption, scattering, and the like of measuring light which has transmitted the reagent layer even if the component is present in the outside of the reagent layer. When the sample is whole blood, each sample gives a different amount of measuring light which enters and is reflected by the reagent layer because of difference in the hematocrit value or the like. When the dry measuring test device has a support or the like, measuring light which transmits the reagent layer is reflected by the support and the reflective light is entered into the reagent layer. This reflective light is unfavorably detected together with the light reflected from the reagent layer. Accordingly, the amount of the reflective light from the support or the like varies depending on, for example, the hematocrit value in the case of whole blood samples, which affects the measured values.

Under these circumstances, in order to realize speedy and highly accurate measurement using a dry measuring test device that determines a substance to be measured in a liquid sample by subjecting the substance to the coloring reaction and determining the degree of coloring in terms of reflectance, it has been desired to develop a method for obtaining sufficiently measurable reflectance corresponding to a low degree of coloring upon measurement of reflectance or a method for reducing influence of absorption and scattering of measuring light attributed to solid matter contained in the liquid sample and of external stray light entered from the opposite side of the surface of the light-measuring site, with maintaining such a structure that the liquid sample penetrates the reagent layer of the dry measuring test device to generate a measurable amount of coloring matter within a short period of time, namely, that the measuring time is so short that influence of dryness can be reduced.

SUMMARY OF THE INVENTION

The present invention has been made in view of the above point, and therefore it has an object of the invention to provide a dry measuring test device for determining a substance to be measured in a liquid sample by subjecting the substance to the coloring reaction and determining the degree of coloring obtained in terms of reflectance, which enables a short period of the measuring time and gives sufficiently measurable reflectance corresponding to a low degree of coloring upon the measurement of reflectance so as to achieve speedy and high accurate measurement. Another object of the invention is to provide a dry measuring test device for determining a substance to be measured in a liquid sample by subjecting the substance to the coloring reaction and determining the degree of coloring obtained in terms of reflectance, which enables a short period of the measuring time and, upon measurement of reflectance, reduces influence of absorption and scattering of measuring light attributed to solid matter contained in the liquid sample and of external stray light entered from the opposite side of the surface of the light-measuring site so as to achieve speedy and high accurate measurement.

As a result of intensive investigation to achieve the above objects, the present inventors found that, in a dry measuring test device for determining a substance to be measured in a liquid sample by subjecting the substance to the coloring reaction and determining the degree of coloring obtained in terms of reflectance, not only rapid penetration of the liquid sample into the reagent layer but also prevention of invasion of red blood cells into the reagent layer can be achieved by providing a reagent layer comprising a reagent containing a chromogen that is reactive with the substance to be measured to develop color and polymer beads embedding light reflective particles as a component of the dry measuring test device.

Further, it was found that, in a dry measuring test device for determining a substance to be measured in a liquid sample by subjecting the substance to the coloring reaction and determining the degree of coloring obtained in terms of reflectance, invasion of solid matter contained in the liquid sample and incidence of external stray light into the reagent layer can be prevented, with maintaining rapid permeability of the liquid sample to the reagent layer, by providing a reagent layer comprising a reagent containing a chromogen that is reactive with the substance to be measured to develop color and a light blocking layer containing light blocking particles, which is laminated on the reagent layer, as a component of the dry measuring test device. Thus, the present invention has been completed.

According to a first aspect of the present invention, there is provided a dry measuring test device, comprising a reagent layer comprising a reagent containing a chromogen and a matrix having the reagent in the form of a layer, for determining a substance to be measured in a liquid sample by measuring the degree of coloring of the chromogen generated through the reaction between the substance and the reagent in terms of reflectance of light entered into the reagent layer, wherein the reagent layer comprises polymer beads embedding light reflective particles.

In the dry measuring test device according to the first aspect of the present invention, the polymer beads which are contained in the reagent layer embeds light reflective particles. Specific examples of the light reflective particles include titanium dioxide, zinc oxide, barium sulfate, magnesium oxide, iron (III) oxide, iron (III) hydroxide, and the like.

The polymer beads embedding the above light reflective particles used in the dry measuring test device of the first aspect of the present invention include those containing as main component a high molecular compound such as: polymer or copolymer having as a main component monomers selected from the group consisting of acrylic acid, methacrylic acid, maleic acid, ester of these substances, styrene, and alkylstyrene; polyurethane; polyurea; polyethylene; polypropylene; and polyvinyl chloride; or the like.

In the dry measuring test device according to the first aspect of the present invention, the polymer beads contained in the reagent layer preferably has the size of about 1 to 40 μm in terms of an average particle diameter.

Further, in the dry measuring test device according to the first aspect of the present invention, the polymer beads preferably contain the light reflective particles in an amount of about 10 to 70 w/v % based on the total amount of the polymer beads. Such polymer beads are preferably contained in the reagent layer in an amount of about 5 to 80 wt % based on the total weight of the reagent layer.

According to a second aspect of the present invention, there is provided a dry measuring test device, comprising a reagent layer comprising a reagent containing a chromogen and a matrix having the reagent in the form of a layer, for determining a substance to be measured in a liquid sample by measuring the degree of coloring of the chromogen generated through the reaction between the substance and the reagent in terms of reflectance of light entered into the reagent layer, wherein a light blocking layer containing light blocking particles is laminated on the reagent layer.

In the dry measuring test device according to the second aspect of the present invention, the light blocking layer contains the light blocking particles which are specifically exemplified by carbon black, iron (II) oxide, iron (II)iron (III) oxide, phthalocyanine blue, phthalocyanine green, and the like.

The specific content of the light blocking particles contained in the light blocking layer of the dry measuring test device of the second aspect of the present invention is preferably about 15 to 90 wt % based on the total weight of the light blocking layer.

Further, in the dry measuring test device according to the second aspect of the present invention, the light blocking layer may contain the light blocking particles as they are. Preferably, the light blocking particles are embedded in the polymer beads and incorporated in the light blocking layer in the form of polymer beads.

In the dry measuring test device according to the second aspect of the present invention, when the polymer beads embedding the light blocking particles are incorporated in the light blocking layer as described above, preferred as the polymer beads are those containing as a main component a high molecular compound such as: polymer or copolymer having as the main component monomers selected from the group consisting of acrylic acid, methacrylic acid, maleic acid, ester of these substances, styrene, and alkylstyrene; polyurethane; polyurea; polyethylene; polypropylene; and polyvinyl chloride; or the like.

In the dry measuring test device according to the second aspect of the present invention in which the polymer beads embedding the light blocking particles are contained in the light blocking layer, the polymer beads preferably contain the light blocking particles in an amount of about 10 to 70 w/v % based on the total amount of the polymer beads. It is preferable to contain such polymer beads in an amount of about 30 to 90 wt % based on the total weight of the light blocking layer. Further, in the dry measuring test device according to the second aspect of the present invention in which the polymer beads embedding the light blocking particles are contained in the light blocking layer, the size of the polymer beads is preferably about 1 to 40 μm in terms of an average particle diameter.

Further, in the dry measuring test device according to the second aspect of the present invention, the reagent layer preferably contains the polymer beads embedding the light reflective particles.

The dry measuring test device of the present invention is described in detail below. First, the dry measuring test device according to a first aspect of the invention is described.

(I) Dry Measuring Test Device According to the First Aspect of the Invention

First explained are the reagent and the polymer beads embedding the light reflective particles both contained in the reagent layer (the layer in which the matrix contains a reagent-containing composition in the form of a layer) of the dry measuring test device according to the first aspect of the present invention. Subsequently, the reagent layer containing them and the dry measuring test device according to the first aspect of the present invention containing the above reagent layer are explained in this order.

(1) Reagent

The reagent contained in the reagent layer of the dry measuring test device according to the first aspect of the present invention comprises a chromogen that can develop color by reacting with the substance to be measured in the liquid sample. Any chromogen may be used as long as the substance to be measured in the liquid sample can be detected by coloring of the chromogen through the reaction between the reagent containing it and the substance to be measured. The term "coloring" used herein means not only color development but also change of color. Further, the "reaction between the substance to be measured and the reagent" includes the case that the substance to be measured itself is a reactant as well as the case that it is involved in the reaction as a catalyst.

The reagent containing the above chromogen varies depending on the type of the substance to be measured and is appropriately selected depending on it. This selection is not particularly different from that for the conventional dry measuring test device.

For example, the dry measuring test device according to the first aspect of the present invention is preferably used for measuring a substance to be measured in body fluid such as blood, urine, saliva, and the like through the coloring reaction based on the oxidation-reduction reaction. In this occasion, the reagent to be preferably used is the one containing oxidase that oxidizes the substance to be measured, a chromogen, and, if required, peroxidase. In the determination of the substance to be measured by the oxidation reaction using oxidase as mentioned above, coloring matter is generated under the condition that the chromogen to be oxidized is directly oxidized by hydrogen peroxide produced through oxidation of the substance to be measured by the action of oxidase, or that the chromogen undergoes oxidation coupling by the action of peroxidase, and the thus-produced coloring matter is colorimetrically measured by means of absorptimetry or luminescence, thereby determining the substance to be measured.

Specific examples of the reagent used in the dry measuring test device according to the first aspect of the present invention include a composition containing glucose oxidase, peroxidase, 4-aminoantipyrine, and MAOS (N-ethyl-N-(2-hydroxy-3-sulfopropyl)-3,5-dimethylaniline) or DAOS (N-ethyl-N-(2-hydroxy-3-sulfopropyl)-3,5-dimethoxyaniline) when the substance to be measured is glucose, a composition containing cholesterol oxidase, peroxidase, 4-aminoantipyrine, and MAOS or DAOS when the substance to be measured is cholesterol, a composition containing lactate dehydrogenase, $NAD^+$, diaphorase, and tetrazolium violet when the substance to be measured is lactic acid, and p-nitrophenyl-phosphate when the substance to be measured is alkaliphosphatase.

The reagent used in the present invention are not limited to those described above, but may be selected depending on the substance to be measured. When the coloring reaction is carried out enzymatically, examples of the enzymes include, in addition to the above-described enzymes, uricase, grycerol-3-phosphate oxidase, choline oxidase, acyl CoA oxidase, sarcosine oxidase, various amino acid oxidase, bilirubin oxidase, lactate oxidase, lactose oxidase, pyruvate oxidase, galactose oxidase, glycerol oxidase, and the like.

Examples of the chromogen include a so-called Trinder's reagent (Ann. Clin. Biochem. 6, 24, 1960) chromogens to be oxidized such as o-anindine, benzidine, o-tridine, or tetramethylbenzidine, and the like.

The above-described enzymes can be the substance to be measured as well as the reagent.

(2) Polymer Beads Embedding Light Reflective Particles

The reagent layer of the dry measuring test device according to the first aspect of the present invention comprises polymer beads embedding the light reflective particles in addition to the above-described reagent. The polymer beads function to give sufficiently measurable reflectance corresponding to a low degree of coloring upon the measurement of the degree of coloring obtained in terms of reflectance of reflective light entered into the reagent layer, when the substance to be measured in the liquid sample is reacted with the reagent to develop color. If the liquid sample contains coloring components like whole blood, the polymer beads also function to prevent the coloring components from invading or transmitting the reagent layer and reduce the influence on the reflective light at the reagent layer.

As the light reflective particles which are contained in the polymer beads used in the present invention, any particles can be used as long as they have such light reflectivity that gives sufficient reflectance corresponding to a low degree of coloring when it is embedded in the polymer beads for use in the dry measuring test device according to the first aspect of the present invention. Specific examples thereof include white pigments such as titanium dioxide, zinc oxide, barium sulfate, or magnesium oxide, colored pigments such as iron (III) oxide (red) or iron (III) hydroxide (red brown or yellow), and the like. Although the color of these light reflective particles are not particularly limited as long as they are particles that reflect the light of the wave length used for the measurement, white light reflective particles are preferably used in the present invention.

As the polymer beads embedding the above-described light reflective particles, any polymer beads can be used as long as they are polymers that can be made into beads and, by embedding the above-described light reflective particles, can give sufficient reflectance corresponding to a low degree of coloring when it is used in the dry measuring test device according to the first aspect of the present invention. Preferable examples thereof include those containing as a main component a high molecular compound, which are comparatively easily made into the form of beads, such as: polymer or copolymer having as a main component hydrophobic vinyl monomers selected from the group consisting of acrylic acid, methacrylic acid, maleic acid, ester of these substances, styrene, alkylstyrene and the like; polyurethane; polyurea; polyethylene; polypropylene; polyvinyl chloride; or the like.

In the dry measuring test device according to the first aspect of the present invention, such polymer beads contain the above light reflective particles in an amount of preferably about 10 to 70 w/v %, more preferably about 20 to 50 w/v %, based on the total amount of the polymer beads. When the substance to be measured in the liquid sample is subjected to the coloring reaction with the reagent and the degree of coloring thus obtained is colorimetrically measured by means of absorptimetry, luminescence, or the like, sufficient reflectance corresponding to a low degree of coloring can be obtained by adjusting the content of the polymer beads to about 5 to 80 wt %, more preferably about 10 to 30 wt %, based on the total weight of the reagent layer in the dry measuring test device according to the first aspect of the present invention.

The particle diameter of the polymer beads used in the present invention ranges preferably from about 1 to 40 $\mu$m, more preferably about 2 to 30 $\mu$m, most preferably about 3 to 15 $\mu$m, in terms of an average particle diameter. If the average diameter of the polymer beads is smaller than 1 $\mu$m, the reagent layer containing them occasionally becomes so dense that the liquid sample hardly penetrates it and the measurement takes long time because penetration and development of the liquid sample proceed slowly. If the average particle diameter of the polymer beads is larger than 40 $\mu$m, they cannot fully prevent coloring components such as blood cells, which interfere the measurement of the degree of coloring, from penetrating the reagent layer.

The polymer beads embedding the light reflective particles used in the present invention can be produced by commonly used methods, for example, the method which comprises adding an appropriate amount of the light reflective particles to the raw material for the polymer beads and polymerizing the material thus obtained under the condition that the resulting polymer is made into the form of beads having an appropriate particle diameter. The polymer beads embedding the light reflective particles as described above are also commercially available and, thus, such products can also be used in the present invention. The commercially available polymer beads embedding the light reflective particles are exemplified by Techpolymer manufactured by Sekisui Kaseihin Kogyo Kabushiki Kaisha and the like.

(3) Reagent Layer

The composition containing the above reagent is retained in the matrix in the form of a layer to constitute the reagent layer. The reagent layer contained in the dry measuring test device according to the first aspect of the present invention contains and stores the above reagent capable of detecting the substance to be measured by developing color through the reaction with the substance to be measured and polymer beads embedding the light reflective particles.

The reagent can be contained in the reagent layer in an amount similar to that in the reagent layer of the conventional dry measuring test device. Namely, it can be an amount sufficient and appropriate to the substance to be measured in the liquid sample absorbed in the dry measuring test device at the measurement. The content of the polymer beads embedding the light reflective particles in the reagent layer is as described above.

In addition to the reagent and the polymer beads embedding the light reflective particles, the reagent layer of the dry measuring test device according to the first aspect of the present invention can contain, if required, a buffer, a hydrophilic high molecular substance, a surface active agent, a plasticizer, a stabilizer, a pretreating agent, and the like, in an appropriate amount.

Examples of the buffer include phosphate buffer, acetate buffer, borate buffer, Tris buffer, Good buffer such as TES (N-Tris(hydroxymethyl)methyl-2-aminoethanesulfonic acid), PIPES (piperidine-1,4-bis (2-ethanesulfonic acid)), and the like. Examples of the hydrophilic high molecular substance include hydroxypropylcellulose, methylcellulose, sodium alginate, polyvinyl alcohol, polyvinyl pyrrolidone, gelatin, modified gelatin, agar, acrylamide polymer, agarose, and the like. It is possible to add to these hydrophilic high molecular substance an emulsion-type adhesive such as Propiofan (BASF) which is copolymer of vinyl propionate and vinyl acetate, latex particles, or the like. Further, specific examples of the surface active agent include Triton X-100, Triton X-405, Tween-20, Tween-80, Brij-35, and the like. As the pretreatment agent, ascorbate oxidase and the like can be used.

As the matrix used to contain and store in the form of a layer the reagent, the polymer beads embedding the light reflective particles, and the above components to be added optionally in the reagent layer of the dry measuring test device according to the first aspect of the present invention, any matrix employed in the commonly used dry measuring test device may be used without any restriction. Examples of the matrix include filter paper, cotton paper, non-woven fabric made of glass fiber or glass fabric, asbest paper, asbest fabric, fabric or non-woven fabric made of synthetic fabric such as nylon, polyester, polystyrene, and the like. As described above, though the hydrophilic high molecular substance can be added to the reagent layer, it can also be a material constituting the matrix by itself. Accordingly, when the reagent layer contains the above hydrophilic high molecular substance, the above-described material such as filter paper or the like is not necessarily used. Further, when filter paper and the like material or the hydrophilic high molecular substance alone is used as the matrix, its thickness ranges preferably from about 5 to 100 $\mu$m.

The reagent, the polymer beads embedding the light reflective particles, and the other components can be contained and retained in the matrix in the form of a layer by the method commonly used. For example, such methods include the direct immersion method which comprises dissolving or dispersing in a liquid the components to be contained, putting the resulting liquid into a tray, and immersing the matrix in it, the method which comprises coating the liquid containing the above various components on a polymer film such as polyethylene telephthalate (hereinafter referred to as "PET") which is easily separated to give a uniform thickness, placing the matrix thereon to allow it to absorb the liquid followed by drying, and separating the matrix from the polymer film, the method of spraying the liquid containing the above various components on the matrix using a spray or the like, and the method of coating the liquid on the matrix with a bar coater or the like. Drying after immersion can be carried out by the commonly used method. In the reagent layer of the dry measuring test device according to the first aspect of the present invention, the drying temperature ranges preferably from 20 to 60° C.

Further, when the matrix is formed by the above hydrophilic high molecular substance alone, it can be carried out by, for example, dissolving or dispersing in a liquid such as water or the like the reagent, the polymer beads embedding the light reflective particles, the hydrophilic high molecular substance, and the other arbitrary components, coating the resulting liquid on a polymer film such as PET or the like to give an appropriate wet thickness, drying it, and separating the matrix from the polymer film. When the reagent layer is formed on the polymer film, the polymer film may be kept if necessary.

As described above, the reagent layer containing in one layer the reagent and the polymer beads embedding the light reflective particles can be obtained. If necessary, the reagent layer may have a two layer structure consisting of the reagent-containing layer and the layer containing the light reflective particle-embedding polymer beads. In this case, each layer can be prepared in accordance with the method for producing the one layer structure as described above. The laminating method may also be carried out by the commonly used method.

(4) Dry Measuring Test Device

As described above, the dry measuring test device according to the first aspect of the present invention comprises the reagent layer in which the reagent capable of reacting with the substance to be measured in the liquid sample to develop color, thereby detecting it, the polymer beads embedding the light reflective particles, and various arbitrary components are retained in the matrix in the form of a layer.

In the dry measuring test device according to the first aspect of the present invention, while the liquid sample is spotted, penetrates, and develops in the reagent layer, the reagent contained in the reagent layer reacts with the substance to be measured in the liquid sample to generate a coloring matter. Upon colorimetrical determination of the degree of coloring thus generated by absorptimetry, luminescence, or the like, the polymer beads embedding the light reflective particles in the reagent layer function to give reflectance sufficient for the measurement. When the liquid sample contains the coloring components such as whole blood, the polymer beads prevent the coloring components from penetrating the reagent layer.

In addition to the above reagent layer, the dry measuring test device according to the first aspect of the present invention may contain, if necessary, members contained in the conventional dry measuring test devices, such as a substrate for supporting the reagent layer, a sample retaining layer that retains the liquid sample, a support to secure space to retain the liquid sample, and the like.

Examples of the substrates for supporting the above reagent layer include a polymer film as described in the production of the above reagent layer, preferably a polymer film capable of transmitting light but not transmitting liquid, such as PET, polypropylene, or the like. If a substrate is a polymer film transmitting light but not transmitting liquid and is laminated on the reagent layer, it is possible to determine the degree of coloring by irradiating light from the side of the substrate without removing from the surface of the reagent layer the excess liquid sample that has not been absorbed by the reagent layer after the liquid sample is spotted on the surface of the reagent layer.

The polymer beads embedding the light reflective particles in the above reagent layer play a role to prevent invasion of the particle components in the liquid sample, such as blood cells, which may enter the reagent layer to reduce sensitivity for measurement of the degree of coloring. If it is possible to measure the degree of coloring from the opposite side of the side where the liquid sample is supplied by using the above substrate, the measurement can be effected more accurately without the influence of the coloring matter such as blood cells since the coloring matter is kept in the supply side.

If the coloring reaction between the substance to be measured in the liquid sample and the reagent is accelerated by the permeation of gas such as oxygen, it is preferable to use as a substrate a porous film which is light-transmissible, liquid-impermeable, and gas-permeable. This is because porosity of the substrate film accelerates the coloring reaction to thereby shorten the reaction time. As to the porous films which are light-transmissible, liquid-impermeable, and gas-permeable, reference can be made to Japanese Examined Patent Publication No. 7-21455 which describes such films in detail. Further, such porous films are commercially available and these can be used in the dry measuring test device according to the first aspect of the present invention. Examples of the commercially available porous films having the above properties include Nuclepore (Nuclepore), Cell Guard (Hoechst Cellanese), Cyclopore (Whatman), and the like.

As the sample retaining layer for retaining the above liquid sample, those having the same construction as the sample retaining layer (which may generally be called the "diffusion layer" or the "developing layer") used in the conventional dry measuring test device can be used.

In the dry measuring test device according to the first aspect of the present invention, it is possible to make space for retaining the liquid sample instead of placing the above sample retaining layer. For this purpose, a support may also be used. The dry measuring test device having the above-mentioned support is exemplified by the one that is constituted by the reagent layer on which the above-described substrate may be laminated and the support for making space to retain the liquid sample, as FIG. 1 shows its sectional view.

Figure 1:
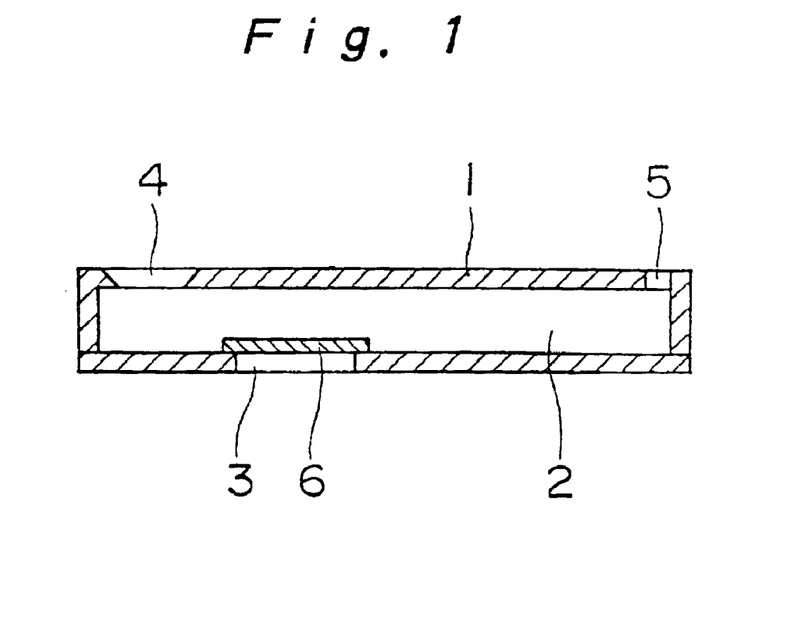
FIG. 1 is a sectional view showing an example of the dry measuring test device according to the first aspect of the present invention.

In FIG. 1, a support 1 has in its inside a capillary compartment 2 for retaining the liquid sample and three holes which connects the capillary compartment with the outside of the support, namely, a light irradiation hole 3 for measuring the degree of coloring, a liquid sample-injecting hole 4, and an air hole 5. A reagent layer 6 is placed in the capillary compartment of the support so as to cover the light irradiation hole 3. If the substrate is laminated on the reagent layer, it is placed so that the measuring light can be irradiated from the side of the substrate. The support in such a dry measuring test device can be constituted by a polymer which is liquid impermeable and does not dissolve in the liquid sample. In the dry measuring test device according to the first aspect of the present invention, it is preferable to give the support light blocking property by, for example, blackening the support. The support having light blocking property can make it possible to reduce the influences of absorbance and scattering of the measuring light by a solid matter in the liquid sample, and external stray light entered from the outside of the support.

Although the dry measuring test device according to the first aspect of the present invention can be used for any method for measuring the substance in the liquid sample, which can generate a coloring matter through the reaction with various reagent, it can be preferably applied to the measurement of the substance contained in body fluids such as blood, urine, saliva, or the like is to be measured through the coloring reaction utilizing oxidation-reduction reaction, for example, the measurement of the content of glucose in blood using the reagent as described in detail above.

If the dry measuring test device according to the first aspect of the present invention as described above is used for the measurement of the substance to be measured in the liquid sample by subjecting the substance to the coloring reaction and determining the degree of coloring in terms of reflectance, it is possible to shorten the measuring time and to obtain sufficiently measurable reflectance corresponding to the low degree of coloring upon the measurement of reflectance. Therefore, quick and highly accurate measurement is enabled.

The dry measuring test device according to a second aspect of the present invention is described below.

(II) Dry Measuring Test Device According to the Second Aspect of the Present Invention First, the reagent layer and the light blocking layer of the dry measuring test device according to the second aspect of the present invention, and then the dry measuring test device having these layers are described.

(1) Reagent Layer

The reagent layer of the dry measuring test device according to the second aspect of the present invention comprises the reagent containing a chromogen that develops color through the reaction with the substance to be measured in the liquid sample in the matrix in the form of a layer. As the reagent, the same reagent as used in the dry measuring test device according to the first aspect of the present invention are exemplified. The content of the reagent in the reagent layer is also the same as in the dry measuring test device according to the first aspect of the present invention. Specifically, the content may be comparable to that of the reagent contained in the reagent layer of the conventional dry measuring test device, namely, a sufficient and appropriate amount to the amount of the substance to be measured in the liquid sample which is absorbed by the dry measuring test device upon measurement.

In the dry measuring test device according to the second aspect of the present invention, the reagent layer preferably contains the light reflective particles as well as the above reagent. More preferably, the light reflective particles are incorporated in the polymer beads, which are contained in the reagent layer. As the polymer beads embedding the light reflective particles, usable are the same polymer beads embedding the light reflective particles used-in the dry measuring test device according to the first aspect of the present invention. The content of the polymer beads embedding the light reflective particles in the reagent layer can also be the same as in the dry measuring test device according to the first aspect of the present invention.

The reagent layer contained in the dry measuring test device according to the second aspect of the present invention is formed by containing in the matrix in the form of a layer the reagent capable of detecting the substance to be measured in the liquid sample through the reaction with the substance to develop color, and preferably the polymer beads embedding the light reflective particles in the amounts as described above, respectively, and, if necessary, the arbitrary components such as a buffer, a hydrophilic high molecular substance, a surface active agent, a plasticizer, a stabilizer, a pretreating agent, or the like, in an appropriate amount. Specific examples of the above arbitrary components are the same as described in the dry measuring test device according to the first aspect of the present invention.

Further, in the reagent layer contained in the dry measuring test device according to the second aspect of the present invention, the matrix used for retaining in the form of a layer the reagent, preferably the polymer beads embedding the light reflective particles, and the various components arbitrarily added is the same as those used in the reagent layer of the dry measuring test device according to the first aspect of the present invention. The reagent, the polymer beads embedding the light reflective particles preferably added, and the other various arbitrary components can be contained and retained in the retaining layer in the form of a layer in the same manner as in the dry measuring test device according to the first aspect of the present invention except that the polymer beads embedding the light reflective particles are arbitrarily added.

Thus, the reagent layer in the dry measuring test device according to the second aspect of the present invention is completely the same as that in the dry measuring test device according to the first aspect of the present invention except that the polymer beads embedding the light reflective particles which are the essential component in the reagent layer of the dry measuring test device according to the first aspect of the present invention are arbitrarily added.

(2) Light Blocking Layer

The dry measuring test device according to the second aspect of the present invention has such a structure that the light blocking layer containing the light blocking particles, preferably the polymer beads embedding the light blocking particles, is laminated on the above-described reagent layer.

As the light blocking particles used in the light blocking layer according to the invention, any particles can be used as long as they show light blocking ability so as to cut the measuring light which is to transmit the reagent layer or the external stray light entered from the opposite side of the surface of the light measuring site when contained in the light blocking layer and used in the dry measuring test device according to the second aspect of the present invention. Preferably used particles are colored pigments including carbon black, iron (II) oxide, iron (II)iron (III) oxide, phthalocyanine blue, phthalocyanine green, and the like.

The light blocking particles in the light blocking layer of the dry measuring test device according to the second aspect of the present invention are preferably contained in an amount of about 15 to 90 wt % based on the total weight of the light blocking layer. The content of the light blocking particles within this range makes it possible to cut the measuring light which is to transmit the reagent layer or the external stray light entered from the opposite side of the surface of the light measuring site.

In the dry measuring test device according to the second aspect of the present invention, the light blocking particles are contained in the light blocking layer, preferably in the state that they are embedded in polymer beads. Such polymer beads are those having the same high molecular compound as a main component as used in the polymer beads embedding the light reflective particles preferably contained in the reagent layer.

When the light blocking particles are contained in the light blocking layer in the dry measuring test device according to the second aspect of the present invention, the above-described polymer beads are preferably used to contain the light blocking particles. A preferable amount of the light blocking particles contained in the polymer beads ranges from about 10 to 70 w/v % based on the total amount of the polymer beads. Further, the dry measuring test device according to the second aspect of the present invention enables blocking of the measuring light which is to transmit the reagent layer or the external stray light entered from the opposite side of the surface of the light measuring part by embedding the above-described polymer beads in an amount of about 30 to 90 wt % based on the total weight of the light blocking layer.

The particle diameter of the polymer beads used in the invention ranges from preferably about 1 to 40 $\mu$m, more preferably about 2 to 30 $\mu$m, further preferably about 3 to 15 $\mu$m, in terms of an average particle diameter. The light blocking layer used in the dry measuring test device according to the second aspect of the present invention is laminated on the reagent layer and the liquid sample is usually applied from the side of the light blocking layer upon measurement. Thus, if the average particle diameter of the polymer beads are smaller than 1 μm, the light blocking layer containing them becomes so dense that the liquid sample hardly permeates it, and the liquid sample permeates and is developed slowly when subjected to the measurement, which may make the measuring time prolonged. Further, the particle diameter of the polymer beads larger than 40 μm is not favorable since colored components, such as blood cells, which affect the measurement of the degree of coloring may possibly permeate the light blocking layer to enter the reagent layer. Thus, when the light blocking particles are contained in the light blocking layer, the use of the polymer beads embedding the light blocking particles is advantageous in that the density and porosity of the light blocking layer can be adjusted to some extent.

Similar to the polymer beads embedding the light reflective particles preferably used in the reagent layer, the polymer beads embedding the light blocking particles used in the invention can be produced by the commonly used methods, for example, the method which comprises adding an appropriate amount of the light blocking particles to the raw material of the polymer beads and polymerizing the resulting mixture under the condition that the polymer to be obtained can be formed into beads having an appropriate particle diameter. Such polymer beads embedding the light blocking particles are commercially available and these products can be used in the present invention. Specifically, the commercially available polymer beads embedding the light blocking particles include Techpolymer manufactured by Sekisui Kaseihin Kogyo Kabushiki Kaisha.

In the dry measuring test device according to the second aspect of the present invention, if necessary, the light blocking layer may contain a buffer, a hydrophilic high molecular substance, a surface active agent, a plasticizer, a stabilizer, a pretreating agent, and the like in an appropriate amount, in addition to the light blocking particles, preferably the polymer beads embedding them. As these components, those described in the above reagent layer can be exemplified.

The light blocking layer of the dry measuring test device according to the second aspect of the present invention can be formed by using only the light blocking particles or the polymer beads embedding the light blocking particles. Preferably, the light blocking particles or the polymer-beads embedding the light blocking particles can be retained in the matrix in the form of a layer to form the light blocking layer. Specifically, appropriate amounts of the light blocking particles or the polymer beads embedding the light blocking particles and the other components may be incorporated in the matrix usually used for the reagent layer and the like in the conventional dry measuring test device by the commonly used method so as to be retained in the form of a layer. The preferable retaining layer used upon preparation of the light blocking layer may be those described as the matrix for the above-described reagent layer. The light blocking particles or the polymer beads embedding the light blocking particles, and the other various components may be incorporated in the above matrix in the form of a layer by the same method as described in the above reagent layer. Preferable thickness of the light blocking layer ranges from 5 to 100 μm.

The thus-obtained light blocking layer is laminated on the reagent layer in the dry measuring test device. according to the second aspect of the present invention. The lamination can be carried out by the commonly used method. For example, the light blocking layer may be formed on the reagent layer which has been coated on a polymer film such as PET or a porous film, depending on the case, followed by drying in the same manner as in the case that the light blocking layer is formed alone. Specifically, the light blocking particles or the polymer beads embedding the light blocking particles, hydrophilic high molecular substance, and various arbitrary components are dissolved or dispersed in a liquid such as water and the resulting liquid is coated or sprayed on the reagent layer followed by drying.

Further, the light blocking layer can be laminated on the reagent layer by placing the liquid matter for forming the reagent layer similar to those used for the preparation of the reagent layer on a polymer film such as PET, or a porous film, depending on the case, placing thereon the liquid matter for forming the light blocking layer, coating these liquid matters on the above film simultaneously using a bar coater or the like, and drying it.

After lamination, the polymer film such as PET or the porous film may be removed if necessary, or used as it is as the dry measuring test device according to the second aspect of the present invention.

The reagent layer of the dry measuring test device according to the second aspect of the present invention may be divided into two layers: the reagent-containing layer; and the layer containing the polymer beads embedding the light reflective particles. When the reagent layer is divided such two layers, lamination of the reagent layer and the light blocking layer can be made in the order of the reagent-containing layer, the layer containing the polymer beads embedding the light reflective particles, and the light blocking layer.

(3) Dry Measuring Test Device

The dry measuring test device according to the second aspect of the present invention comprising the reagent layer formed by retaining the reagent capable of reacting the substance to be measured in the liquid sample to develop color thereby detecting it, the polymer beads embedding the light reflective particles which are preferably used in the invention, and various arbitrary components in the matrix in the form of a layer is characterized by having laminated on the reagent layer the light blocking layer containing the light blocking particles, preferably the polymer beads embedding the light blocking particles.

In the dry measuring test device according to the second aspect of the present invention, the liquid sample is spotted on the light blocking layer laminated on the reagent layer and a coloring matter is generated by the reaction between the reagent contained in the reagent layer and the substance to be measured in the liquid sample during penetration and development of the sample in the light blocking layer and the reagent layer. When the degree of coloring of the thus-generated coloring matter is colorimetrically determined by absorptimetry, luminescence, or the like, the light blocking layer functions to cut the measuring light which is to transmit the reagent layer or the external stray light entered from the opposite side of the surface of the light measuring part, which enables accurate determination. Further, the light blocking layer prevents the coloring matter such as blood cells from invading the reagent layer and from absorbing and scattering the measuring light in the reagent layer.

The dry measuring test device according to the second aspect of the present invention may have members used in the conventional dry measuring test device if necessary in addition to the reagent layer and the light blocking layer laminated thereon, for example, a substrate for supporting the reagent layer, a sample retaining layer capable of retaining the liquid sample, a support for making space to retain the liquid sample, and the like.

Examples of the substrates for supporting the above reagent layer include a polymer film as described in the production of the above reagent layer, preferably a polymer film capable of transmitting light but not transmitting liquid, such as PET, polypropylene, or the like. If a substrate is a polymer film transmitting light but not transmitting liquid and is laminated on the reagent layer on the opposite side where the light blocking layer is laminated, it is advantageous to determine the degree of coloring by irradiating light from the side of the substrate.

In the case of the coloring reaction between the substance to be measured in the liquid sample and the reagent which is accelerated by the permeation of gas such as oxygen, a preferably used a substrate is a porous film which is light transmissible, liquid impermeable, and gas permeable. This is because porosity of the substrate film accelerates the coloring reaction to shorten the reaction time. Usable as the porous films which are light transmissible, liquid impermeable, and gas permeable are those described for the porous film used in the dry measuring test device according to the first aspect of the present invention.

In the dry measuring test device according to the second aspect of the present invention, the sample retaining layer for retaining the liquid sample can be laminated in the order of the reagent layer, the light blocking layer, and the sample retaining layer, or the order of the reagent layer, the sample retaining layer, and the light blocking layer. As such a sample retaining layer, those having the same construction as the sample retaining layer (which may generally be called the "diffusion layer" or the "developing layer") used in the conventional dry measuring test device can be used.

In the dry measuring test device according to the second aspect of the present invention, it is possible to make space for retaining the liquid sample instead of placing the above sample retaining layer. For this purpose, a support may also be used. The dry measuring test device having the support as described above is exemplified by the one that is constituted by the light blocking layer laminated reagent layer on which the above-described substrate may also be laminated and the support for making space to retain the liquid sample, as FIG. 2 shows its sectional view.

Figure 2:
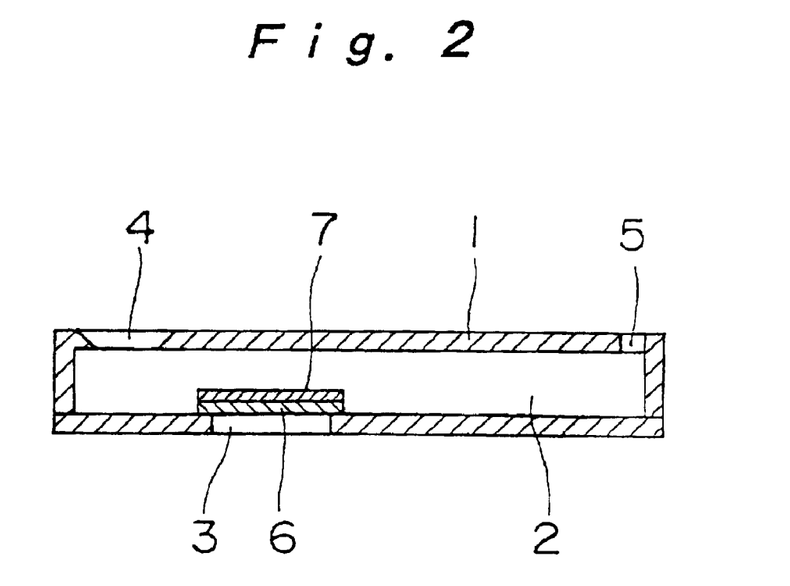
FIG. 2 is a sectional view showing an example of the dry measuring test device according to the second aspect of the present invention.

In FIG. 2, a support 1 has a capillary compartment 2 for retaining the liquid sample inside and three holes which connects the capillary compartment with the outside of the support, namely, a light irradiation hole 3 for measuring the degree of coloring, a liquid sample-pouring hole 4, and an air hole 5. A reagent layer 6 on which a light blocking layer 7 is laminated, is placed in the capillary compartment of the support so that it covers the light irradiation hole 3 and that the light blocking layer faces the capillary compartment. If the substrate is laminated on the reagent layer, it is placed so that the measuring light is irradiated from the side of the substrate. The support in such a dry measuring test device can be constituted by a polymer which is liquid impermeable and does not dissolve in the liquid sample.

Similar to the dry measuring test device according to the first aspect of the present invention, although the dry measuring test device according to the second aspect of the present invention can be used for any method for measuring the substance in the liquid sample, which can generate coloring matter through the reaction with various reagent, it can be preferably applied to the measurement of the substance contained in body fluids such as blood, urine, saliva, or the like is to be measured through the coloring reaction utilizing oxidation-reduction reaction, for example, the measurement of the content of glucose in blood using the reagent as described in detail above.

If the dry measuring test device according to the second aspect of the present invention as described above is used for measuring the substance to be measured in the liquid sample by subjecting the substance to the coloring reaction and determining the degree of coloring in terms of reflectance, it is possible to shorten the measuring time and to reduce the influence by the solid matter in the liquid sample which absorbs and scatter the measuring light and the influence of the external stray light entered from the opposite side of the surface of the light measuring part upon the measurement of reflectance. Therefore, quick and highly accurate measurement is enabled.

DESCRIPTION OF THE PREFERRED EMBODIMENTS

Examples of the present invention are demonstrated below.

Example 1

Dry Measuring Test Device According to the First Aspect of the Present Invention
[Preparation of Dry Measuring Test Device According to the First Aspect of the Present Invention]

Each component was mixed to give a composition as shown in Table 1 to prepare the coating liquid for the reagent layer. Cell Guard (Hoechst Cellanese) used for the matrix of the reagent layer was attached on a glass plate so as to form no wrinkle. The above coating liquid was coated on the resulting Cell Guard using a knife coater to give a thickness of 50 $\mu$m and dried at 25° C. and at a humidity of 15% for 30 minutes to form the reagent layer. Then, the reagent layer with Cell Guard was peeled from the glass plate and cut into the size of 7 mm×7 mm.

The resulting reagent layer with Cell Guard having a size of 7 mm square was attached on a PET film having a size of 30 mm×7 mm with a hole of a diameter of 4 mm (a measuring light irradiation hole) so that the side of Cell Guard could face the PET film to cover the hole. A cover was attached on the reagent layer side of the PET film with a thermoplastic resin so as to form the capillary compartment between the cover and the PET film. Therefore, an example of the dry measuring test device according to the first aspect of the present invention was prepared. The cover used herein had the liquid sample-supplying hole and the air hole. (cf. FIG. 1)

For comparison, the dry measuring test device of Comparative Example 1 was prepared in the same manner as in Example 1 except for using the light reflective particles (titanium dioxide) which were contained in the polymer beads (Techpolymer MBX-5/White) in place of the light reflective particle-embedding polymer beads used in the coating liquid for the reagent layer.

TABLE 1

| Composition | Component | |
|---|---|---|
| | Example 1 | Comparative Example 1 |
| Borate buffer (150 mM, pH 7.0) | 29.0 g | 29.0 g |
| Hydroxypropyl cellulose | 1.3 g | 1.3 g |
| Techpolymer MBX-5/White | 5.0 g | — |
| Titanium dioxide | — | 2.7 g |
| Propiofan (BASF) | 1.3 g | 1.3 g |
| TES buffer (300 mM, pH 7.0) | 5.0 g | 5.0 g |
| Tween-20 (50 wt %) | 3.2 g | 3.2 g |
| Glucose oxidase | 138 ku | 138 ku |
| Peroxidase | 103 ku | 103 ku |
| 4-Aminoantipyrine | 0.2 g | 0.2 g |
| MAOS (Dojin) | 0.5 g | 0.5 g |
| Distilled water | 2.4 g | 4.6 g |

In Table 1 above, Techpolymer MBX-5/White (Sekisui Kaseihin Kogyo) is polymer beads of true sphere crosslinked polymethylmethacrylate having an average particle size of 5 μm in which each bead contains titanium dioxide in an amount of 50 w/v %.

[Evaluation of Dry Measuring Test Device According to the First Aspect of the Present Invention]

The dry measuring test devices obtained in Example 1 and Comparative Example 1 were tested for permeability and the reaction rate.

(1) Permeability Test

Figure 3:
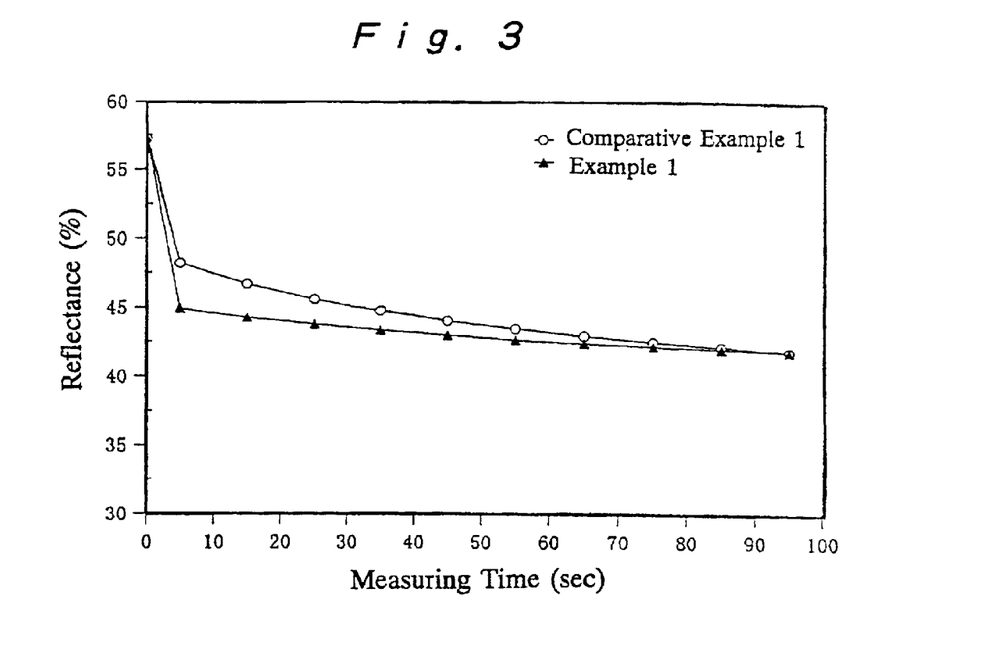
FIG. 3 shows a time-course change of reflectance measured at 640 nm of a specimen, which was prepared by subjecting whole blood to glycolysis and adding thereto food color blue No. 1, using the dry measuring test devices obtained in Example 1 and Comparative Example 1 of the present invention.

After whole blood was allowed to stand at room temperature for one day for glycolysis, food colorant blue No. 1 was added thereto in an arbitrary amount and the hematocrit value was adjusted to 68%. Thus, sample I was obtained. 10 μl of sample I was introduced into the reagent layer of the dry measuring test device obtained in Example 1 through the liquid sample-supplying hole. From 5 seconds later, light of 640 nm was irradiated from the side of Cell Guard through the measuring light-irradiation hole and obtained reflectance was measured using a reflectiometer (color-difference meter) in the passage of time at 10-second intervals for 125 seconds. The same test was carried out for the dry measuring test device obtained in Comparative Example 1. FIG. 3 shows the results of time-course change of reflectance measured for sample I using the dry measuring test devices obtained in Example 1 and Comparative Example 1. In FIG. 3, the axis of ordinate and the axis of abscissa stands for reflectance (%) and the measuring time (sec), respectively.

(2) Reaction Rate Test

Figure 4:
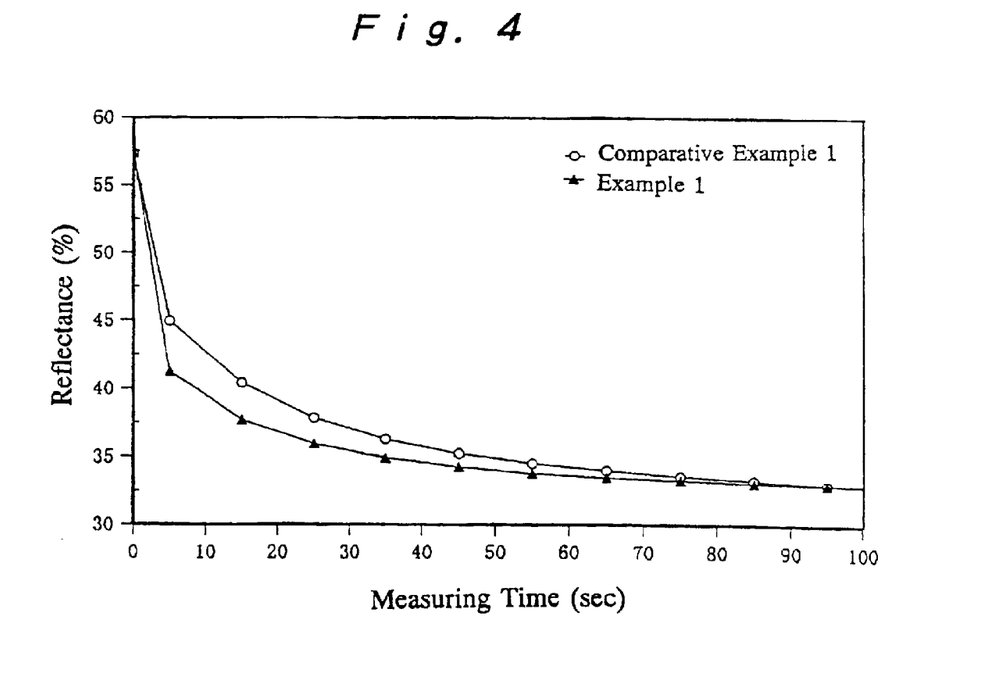
FIG. 4 shows the time-course change of reflectance measured at 640 nm of a whole blood specimen using the dry measuring test devices obtained in Example 1 and Comparative Example 1 of the present invention.

Whole blood (glucose concentration: 99 mg/dl) supplemented with a glycolysis inhibitor (NaF) was adjusted to have a hematocrit value of 68% to serve as sample II. 10 μl of sample II was introduced into the reagent layer of the dry measuring test device obtained in Example 1 through the liquid sample-supplying hole. From 5 seconds later, light of 640 nm was irradiated from the side of Cell Guard through the measuring light-irradiation hole and obtained reflectance was measured using a reflectiometer (color-difference meter) at 10-second intervals for 125 seconds. The same test was carried out for the dry measuring test device obtained in Comparative Example 1. FIG. 4 shows the results of time-course change of reflectance measured for sample II using the dry measuring test devices obtained in Example 1 and Comparative Example 1. In FIG. 4, the axis of ordinate and the axis of abscissa stands for reflectance (%) and the measuring time (sec), respectively.

As apparent from these results, the sample liquid permeated the reagent layer well and, actually, the reaction rate of the reaction between the reagent and the substance to be measured was high in the dry measuring test device obtained in Example 1 as compared with the conventional dry measuring test device (Comparative Example 1) containing titanium dioxide as a reflective member.

EXAMPLE 2

Dry Measuring Test Device According to the Second Aspect of the Present Invention

[Preparation of Dry Measuring Test Device According to the Second Aspect of the Present Invention]

Each component for the reagent layer was mixed to give a composition as shown in Table 2 to prepare the coating liquid for the reagent layer. Cell Guard (Hoechst Cellanese) was attached on a glass plate so as to form no wrinkle. The above coating liquid was coated on the resulting Cell Guard using a knife coater to give a thickness of 100 μm and dried at 25° C. and at a humidity of 15% for 30 minutes to form the reagent layer. Further, each component for the light blocking layer was mixed to give a composition as shown in Table 2 to prepare the coating liquid for the light blocking layer. The resulting coating liquid was coated on the above reagent layer using a knife coater to give a thickness of 40 μm and dried at 25° C. and at a humidity of 15% for 30 minutes to form the light blocking layer. Then, the reagent layer on which the light blocking layer was laminated (hereinafter sometimes referred to as "the light blocking layer/reagent layer") with Cell Guard was peeled from the glass plate and cut into the size of 7 mm×7 mm.

The resulting light blocking layer/reagent layer with Cell Guard having a size of 7 mm square was attached by heat press on a PET film having a size of 30 mm×7 mm with a hole of a diameter of 4 mm so that the side of Cell Guard could face the PET film to cover the hole. A cover was attached on the light blocking layer/reagent layer side of the PET film with a thermoplastic resin so as to form the capillary compartment between the cover and the PET film. Therefore, an example of the dry measuring test device according to the second aspect of the present invention was prepared. The cover used herein had the liquid sample-supplying hole and the air hole. (cf. FIG. 2)

For comparison, the dry measuring test device of Comparative Example 2 was prepared in the same manner as in Example 2 except for using the reagent layer on which no light blocking layer was laminated in place of the light blocking layer/reagent layer. The dry measuring test device of Comparative Example 2 was used for comparison in the dry measuring test device according to the second aspect of the present invention, but it corresponded to the invention product in the dry measuring test device according to the first aspect of the present invention. Since this dry measuring test device was prepared herein for comparison in the dry measuring test device according to the second aspect of the present invention, the term "Comparative Example 2" was applied to this dry measuring test device.

TABLE 2

| Composition | Component Reagent layer | Light blocking layer |
|---|---|---|
| Borate buffer (150 mM, pH 7.0) | 29.0 g | — |
| Hydroxypropyl cellulose | 1.3 g | 1.3 g |
| Techpolymer MBX-5/White | 5.0 g | — |
| Techpolymer MBX-5/Black | — | 5.0 g |
| Propiofan (BASF) | 1.3 g | 1.3 g |
| TES buffer (300 mM, pH 7.0) | 5.0 g | 2.5 g |
| Tween-20 (50 wt %) | 3.2 g | 3.2 g |
| Glucose oxidase | 138 ku | — |
| Peroxidase | 103 ku | — |
| 4-Aminoantipyrine | 0.2 g | — |
| MAOS (Dojin) | 0.5 g | — |
| Distilled water | 2.4 g | 38.6 g |

In Table 2 above, Techpolymer MBX-5/White (Sekisui Kaseihin Kogyo) is polymer beads of true sphere crosslinked polymethylmethacrylate having an average particle size of 5 µm in which each bead contains titanium dioxide in an amount of 50 w/v % and Techpolymer MBX-5/Black (Sekisui Kaseihin Kogyo) is polymer beads of true sphere crosslinked polymethylmethacrylate having an average particle size of 5 µm in which each bead contains carbon black in an amount of 50 w/v %.

[Evaluation of Dry Measuring Test Device According to the Second Aspect of the Present Invention]

The dry measuring test devices obtained in Example 2 and Comparative Example 2 were tested for the influence of the difference of hematocrit value of the whole blood sample on the measured value.

Figure 5:
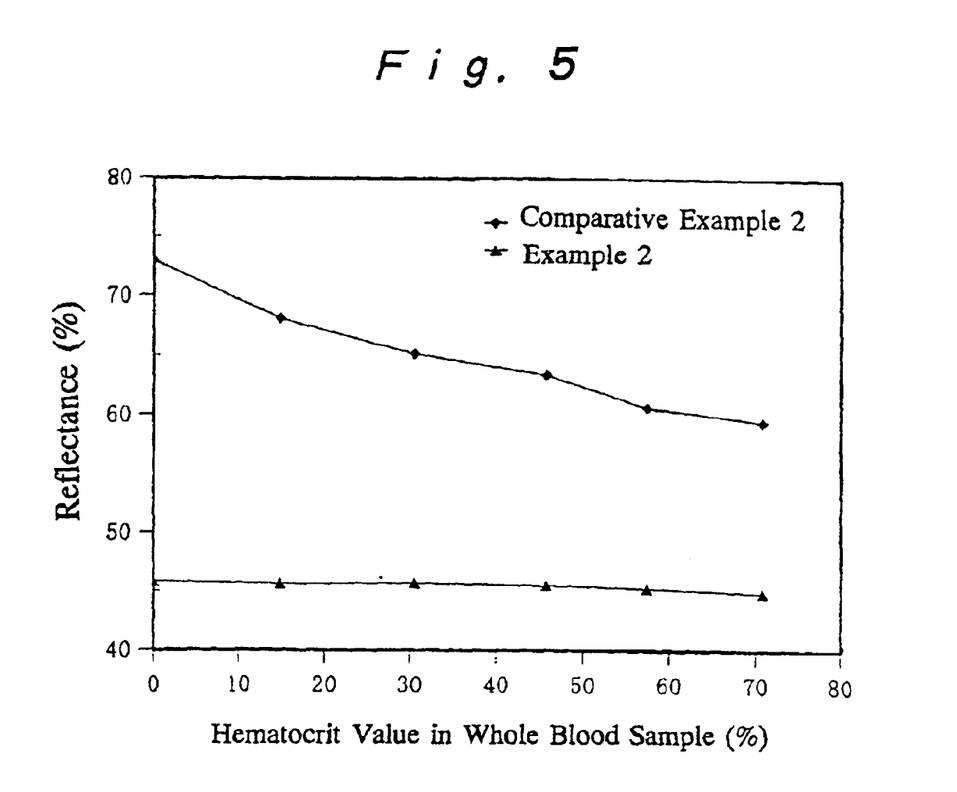
FIG. 5 shows reflectances of various specimens different in the hematocrit value measured at 640 nm using the dry measuring test devices obtained in Example 2 and Comparative Example 2 of the present invention.

Whole blood (glucose concentration: 99 mg/dl) supplemented with a glycolysis inhibitor (NaF) was adjusted to have a different hematocrit value (0%, 15%, 31%, 46%, 57%, and 71%) to prepare six samples. 10 µl of each sample was spotted on the reagent layer of the dry measuring test device obtained in Example 2. From 5 seconds later, light of 640 nm was irradiated from the side of Cell Guard through the measuring light-irradiation hole and obtained reflectance was measured using a reflectiometer (color-difference meter). The same test was carried out for the dry measuring test device obtained in Comparative Example 2. FIG. 5 shows the results of measurement of reflectance of the above samples using the dry measuring test devices obtained in Example 2 and Comparative Example 2. In FIG. 5, the axis of ordinate and the axis of abscissa stand for reflectance (%) and the hematocrit value (%), respectively.

As apparent from these results, the reflectance does not change if the hematocrit value is changed in the dry measuring test device obtained in Example 2. In other words, it was found that the substance to be measured in whole blood could be determined accurately regardless of the amount of the blood cell components.

What is claimed is:

1. A dry measuring test device, comprising a reagent layer comprising a reagent containing a chromogen and a matrix which retains said reagent in the form of a layer, for determining a substance to be measured in a liquid sample by measuring the degree of coloring of the chromogen generated through the reaction between the substance to be measured and the reagent in terms of reflectance of light entered into the reagent layer, wherein a light blocking layer containing light blocking particles in the form of polymer beads embedding the light blocking particles is laminated on the reagent layer, wherein the light blocking particles are carbon black.

2. The dry measuring test device as claimed in claim 1, wherein the light blocking particles are contained in an amount of 15 to 90 wt % based on the total weight of the light blocking layer.

3. The dry measuring text device as claimed in claim 1, wherein said polymer beads contain as a main component a compound selected from the group consisting of: polymer or copolymer having as a main component monomers selected from the group consisting of acrylic acid, methacrylic acid, maleic acid, ester of these substances, styrene, and alkylstyrene; polyurethane; polyurea; polyethylene; polypropylene; and polyvinyl chloride.

4. The dry measuring test device as claimed in claim 1, wherein the light blocking particles are contained in an amount of 10 to 70 w/v % based on the total content of the polymer beads, and the polymer beads are contained in the light blocking layer in an amount of 30 to 90 wt % based on the total weight of the light blocking layer.

5. The dry measuring device as claimed in claim 1, wherein an average particle diameter of the polymer beads ranges from 1 to 40 µm.

6. The dry measuring test device as claimed in claim 1, wherein the reagent layer further contains polymer beads embedding the light reflective particles.

* * * * *

UNITED STATES PATENT AND TRADEMARK OFFICE
Certificate

Patent No. 6,905,653 B1                          Patented: June 14, 2005

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Yoshihiko Higuchi, Kyoto (JP); and Michio Naka, Kyoto, (JP).

Signed and Sealed this Twelfth Day of June 2007.

*JILL A. WARDEN*
*Supervisory Patent Examiner*
*Art Unit 1743*